(12) United States Patent
Yamada et al.

(10) Patent No.: US 8,773,658 B2
(45) Date of Patent: Jul. 8, 2014

(54) DETECTION DEVICE

(75) Inventors: Kohei Yamada, Minowa (JP); Yoshifumi Hano, Suwa (JP)

(73) Assignee: Seiko Epson Corporation (JP)

( * ) Notice: Subject to any disclaimer, the term of this patent is extended or adjusted under 35 U.S.C. 154(b) by 142 days.

(21) Appl. No.: 13/455,516

(22) Filed: Apr. 25, 2012

(65) Prior Publication Data

US 2012/0274935 A1    Nov. 1, 2012

(30) Foreign Application Priority Data

Apr. 27, 2011 (JP) .................................. 2011-099243

(51) Int. Cl.
*G01J 3/44* (2006.01)
*G01N 21/00* (2006.01)
*E03B 1/00* (2006.01)
*F17D 1/00* (2006.01)
*F17D 3/00* (2006.01)

(52) U.S. Cl.
USPC .............................. 356/301; 422/82.05; 137/2

(58) Field of Classification Search
USPC ................. 356/301, 445, 436, 440–442, 447; 422/63, 67, 68.1, 69, 82.05, 82.08; 436/43, 50, 52, 164, 167, 171
See application file for complete search history.

(56) References Cited

U.S. PATENT DOCUMENTS

| | | | |
|---|---|---|---|
| 5,328,851 A * | 7/1994 | Zaromb | 436/178 |
| 6,649,416 B1 * | 11/2003 | Kauer et al. | 436/164 |
| 6,943,032 B2 | 9/2005 | Farquharson et al. | |
| 7,133,129 B2 | 11/2006 | Lee et al. | |
| 7,212,284 B2 | 5/2007 | Deng et al | |
| 7,462,492 B2 | 12/2008 | Farquharson et al. | |
| 8,012,763 B2 | 9/2011 | Shende et al. | |
| 2004/0191920 A1 | 9/2004 | Farquharson et al. | |
| 2007/0108126 A1 | 5/2007 | Lee | |
| 2009/0143659 A1 * | 6/2009 | Li et al. | 600/345 |
| 2010/0053605 A1 | 3/2010 | Ragucci et al. | |
| 2010/0101983 A1 * | 4/2010 | Butler et al. | 209/552 |
| 2010/0116021 A1 | 5/2010 | O'Brien | |
| 2010/0267013 A1 | 10/2010 | Su et al. | |
| 2011/0311978 A1 * | 12/2011 | Makarewicz et al. | 435/6.12 |
| 2011/0317159 A1 | 12/2011 | Shende et al. | |

FOREIGN PATENT DOCUMENTS

| | | |
|---|---|---|
| JP | 2000-356587 | 12/2000 |
| JP | 2005-265634 | 9/2005 |
| JP | 3714671 | 9/2005 |
| JP | 2006-003285 | 1/2006 |

(Continued)

*Primary Examiner* — Gregory J Toatley
*Assistant Examiner* — Willie Merrell, II
(74) *Attorney, Agent, or Firm* — Harness, Dickey & Pierce, P.L.C.

(57) ABSTRACT

A detection device includes a sensor chip, a suction section adapted to suck a fluid sample to the sensor chip, a light source adapted to irradiate the sensor chip, a light intensity adjustment section adapted to adjust intensity of the light, a light detection section adapted to detect the light reflecting the sample adsorbed to the sensor chip, and a control section adapted to perform drive control on the suction section. The control section sets the suction flow velocity to V1 in the first mode in which the light detection section performs the detection, and sets the suction flow velocity to V2 (V2>V1) in the second mode. The light intensity adjustment section sets the light intensity to L1 in the first mode, and sets the light intensity to L2 (L2>L1) in the second mode. The first and second modes are switched based on the signal from the light detection section.

11 Claims, 12 Drawing Sheets

(56) References Cited

FOREIGN PATENT DOCUMENTS

| | | | |
|---|---|---|---|
| JP | 2006-258636 A | 9/2006 | |
| JP | 2006-266906 A | 10/2006 | |
| JP | 2007-078620 | 3/2007 | |
| JP | 2007-101476 | 4/2007 | |

* cited by examiner

SERS SPECTRUM OF TMT MOLECULES

DETECTION DEVICE

BACKGROUND

1. Technical Field

The present invention relates to a detection device.

2. Related Art

In recent years, as one of sensitive spectroscopic techniques for detecting low-density sample molecules, surface enhanced Raman scattering (SERS) spectroscopy using surface plasmon resonance (SPR), in particular localized surface plasmon resonance (LSPR), has been attracting attention (Japanese Patent No. 3714671, JP-A-2000-356587). The SERS denotes a phenomenon that the Raman scattering light is enhanced $10^2$ through $10^{14}$ times on a metal surface having a structure of providing unevenness in nanometer scale. The sample molecules are irradiated with an excitation light with a single wavelength such as a laser. The light with a scattering wavelength (the Raman scattering light) slightly shifted from the wavelength of the excitation light as much as the molecular vibration energy of the sample molecules is spectroscopically detected to thereby obtain the fingerprint spectrum of the sample molecules. It becomes possible to identify the sample molecules based on the shape of the fingerprint spectrum.

The surface plasmon resonance sensor of this kind is formed by fixing metal fine particles made of, for example, gold or silver on a substrate. The detection device provided with this sensor irradiates the sample molecules adsorbed to the metal nanoparticles of the surface plasmon resonance sensor with light, and then detects the Raman scattering light thus enhanced.

Here, as one of the usages of the surface plasmon resonance sensor, there is cited, for example, monitoring of an environmental pollutant. In order to monitor the pollutant, it is required to detect the pollutant continuously in real time. However, according to the detection device described above, although it is possible to detect whether or not the sample molecules adsorbed to the metal nanoparticles of the surface plasmon resonance sensor are pollutants, the detection can be performed only once. Therefore, if the presence or absence of the sample molecules in space is detected a number of times in real time, for example, it is not achievable to detect whether or not the sample molecules surely exist at a density equal to or higher than a certain level, or whether or not the density at which the sample molecules exist is surely equal to or lower than a certain level with improved reliability. Therefore, the detection device capable of performing highly reliable and continuous measurement have been demanded. It should be noted that the continuous measurement denotes that, assuming that a measurement period is formed by combining a cleaning period and an object detection period with each other, the measurement periods are contiguous.

SUMMARY

An advantage of some aspects of the invention is to solve at least a part of the problems described above, and the invention can be implemented as the following forms or application examples.

Application Example 1

This application example is directed to a detection device including a sensor chip, a suction section adapted to suck a fluid sample including a sample molecule to thereby adsorb the fluid sample to the sensor chip, a light source adapted to irradiate the sensor chip with light, a light intensity adjustment section adapted to adjust intensity of the light irradiating the sensor chip, a light detection section adapted to detect the sample molecule using light reflecting the sample molecule adsorbed on the sensor chip, and a control section adapted to control the suction section and the light intensity adjustment section, and assuming that a flow velocity of the fluid sample on the sensor chip in a first mode including a period in which the light detection section performs the detection is V1, and the flow velocity of the fluid sample on the sensor chip in a second mode is V2, the suction section controls the flow velocity of the fluid sample so that V2>V1 is fulfilled, assuming that the intensity of the light on the sensor chip from the light source in the first mode is L1, and the light intensity on the sensor chip in the second mode is L2, the light intensity adjustment section controls the light intensity so that L2>L1 is fulfilled, and the control section switches between the first mode and the second mode based on a signal from the light detection section.

According to this application example, it is possible to adsorb the sample molecules in the fluid sample sucked at the flow velocity V1 to the sensor chip in the first mode. If the sensor chip is irradiated with the light from the light source with the light intensity L1 in the first mode, the light reflecting the sample molecules adsorbed to the sensor chip is generated. The light detection section is capable of detecting the light from the sensor chip. On the other hand, in the second mode, the flow velocity is set to V2 higher than V1 in the first mode, and the light intensity is set to L2 higher than L1. Therefore, in the second mode, it is possible to efficiently desorb the sample once adsorbed to the sensor chip due to the thermal energy derived from application of the light energy and the flowing force of the fluid sample.

As described above, by performing the first mode and the second mode alternately, the sample once adsorbed to the sensor chip can be made to desorb therefrom. In such a manner, it is possible to clean up the sensor chip after the inspection, and it becomes possible to repeatedly perform the subsequent inspection without leaving the influence of the previous inspection. Therefore, by switching between the first mode and the second mode, continuous inspection becomes possible. Moreover, it is possible to clean up the sensor chip after the inspection. Further, since switching between the first mode and the second mode is performed based on the signal from the light detection section, continuous measurement with high reliability can be performed. It should be noted that the continuous measurement denotes that, assuming that a measurement period is formed by combining the first mode and the second mode with each other, the measurement periods are contiguous.

Application Example 2

In the detection device according to the application example described above, it is preferable that the sensor chip generates Raman scattering light of the fluid sample, and the optical detection section detects the Raman scattering light of an inspection target material, which can exist in the fluid sample.

According to this configuration, the Raman scattering light is a signal reflecting the inspection target material, and it is possible to determine whether or not the inspection target material exists in the fluid sample.

Application Example 3

In the detection device according to the application example described above, it is preferable that the light intensity adjustment section includes an optical filter, and adjusts the light intensity by switching the optical filter.

According to this configuration, the light intensity is adjusted by switching between the filters with different transmission. On this occasion, the intensity of the light passing through the light intensity adjustment section can easily be changed by mechanically controlling the light transmission of the filter.

Application Example 4

In the detection device according to the application example described above, it is preferable that the suction section includes a negative pressure generation section, and the control section controls the drive condition of the negative pressure generation section.

According to this configuration, by performing the adjustment control on the drive condition of the negative pressure generation section such as the fluid transport amount per unit time, the flow velocity of the fluid sample on the sensor chip can be controlled.

Application Example 5

In the detection device according to the application example described above, it is preferable that the control section compares a level of the signal output by the light detection section with a first determination level, and when the level of the signal exceeds the first determination level, the control section performs switching from the first mode to the second mode.

According to this configuration, the sample molecules in the fluid sample sucked therein are adsorbed to the sensor chip in the first mode, and the intensity of the signal from the light detection section increases in conjunction therewith. The inspection of presence or absence of the sample molecule can be performed before the signal level reaches the first determination level. Further, if the level of the signal from the light detection section exceeds the first determination level, switching from the first mode to the second mode is performed. Then, in the second mode, the sample molecules thus adsorbed are desorbed. Therefore, it is possible to determine the time for starting the clean-up of the sensor chip.

Application Example 6

In the detection device according to the application example described above, it is preferable that the control section performs switching from the second mode to the first mode when the level of the signal from the light detection section falls below a second determination level. According to this configuration, the sample molecules thus adsorbed are desorbed from the sensor chip in the second mode. If the level of the signal from the light detection section is equal to or lower than the second determination level, it is determined that the desorption is sufficiently performed, and the second mode is terminated to make a transition to the first mode. Therefore, it is possible to determine the time for ending the clean-up of the sensor chip.

Application Example 7

In the detection device according to the application example described above, it is preferable that a supply section adapted to supply the sensor chip with a reference sample via the fluid sample in the first mode is further provided, the light detection section detects light reflecting the reference sample at a wavelength different from that of the inspection target material, which can exist in the fluid sample, and the control section performs switching from the first mode to the second mode when a level of the signal reflecting the reference sample exceeding a third determination level despite the signal reflecting the inspection target material is lower than the first determination level.

According to this configuration, the time for making the transition from the first mode to the second mode is determined by performing the control based on the comparison between the signal reflecting the reference sample and the third determination level in parallel. Therefore, it is possible to determine the time for making the transition from the first mode to the second mode even in the case in which the sample molecules do not exist or only infinitesimal quantity thereof exists in normal cases like trinitrotoluene (TNT) molecules.

Application Example 8

In the detection device according to the application example described above, it is preferable that the control section performs switching from the second mode to the first mode when a signal level from the light detection section corresponding to the reference sample falls below a fourth determination level despite the level of the signal from the light detection section corresponding to the sample molecule as the inspection target is higher than the second determination level.

According to this configuration, the time for making the transition from the second mode to the first mode is determined by performing the control based on the comparison between the signal reflecting the reference sample and the fourth determination level in parallel. Therefore, it is possible to determine the time for making the transition from the second mode to the first mode even in the case in which the sample molecules do not exist or only infinitesimal quantity thereof exists in normal cases like trinitrotoluene (TNT) molecules.

Application Example 9

In the detection device according to the application example described above, it is preferable that the supply section can supply a constant amount of the reference sample during the first mode.

According to this configuration, a constant amount of the reference sample is supplied from the supply section into the fluid sample. By setting the total amount of the reference sample to the constant amount, switching from the first mode to the second mode can be performed with accuracy. As a result, an appropriate time for detecting the inspection target material can be allocated to the first mode even in the case in which the concentration of the inspection target material is too low to be detected.

Application Example 10

In the detection device according to the application example described above, it is preferable that the reference sample can be set to a molecule including at least one of a hetero ring, a benzene ring, a COOH group, an OH group, a CHO group, an S atom, and an N atom.

According to this configuration, these groups and atoms can adhere or be bonded to metals with relative ease, and the molecules can surely be detected. Therefore, the molecules can be made to function as the reference sample.

Application Example 11

In the detection device according to the application example described above, it is preferable that the control section at least switches between the second mode and the first mode in a repeated manner.

According to this configuration, the sensor chip is thus cleaned up in the second mode performed prior to the first mode. Thus, the detection accuracy of the detection device can be improved. Further, due to the second mode performed after the first mode, it is possible to clean up the sensor chip prior to the subsequent detection of the sample molecules. Therefore, the detection of the sample molecules can continuously be performed with good accuracy.

BRIEF DESCRIPTION OF THE DRAWINGS

The invention will be described with reference to the accompanying drawings, wherein like numbers reference like elements.

DESCRIPTION OF AN EXEMPLARY EMBODIMENT

Hereinafter, an embodiment of the invention will be described in detail with reference to the accompanying drawings. It should be noted that in each of the following drawings, the scale sizes of the members are made different from the actual dimensions in order for expressing the members as those with recognizable dimensions. It should be noted that the embodiments explained below do not unreasonably limit the content of the invention as set forth in the appended claims, and all of the constituents set forth in the embodiments are not necessarily essential as means of the invention for solving the problems.

Embodiment

1. Basic Configuration of Detection Device

Figure 1:
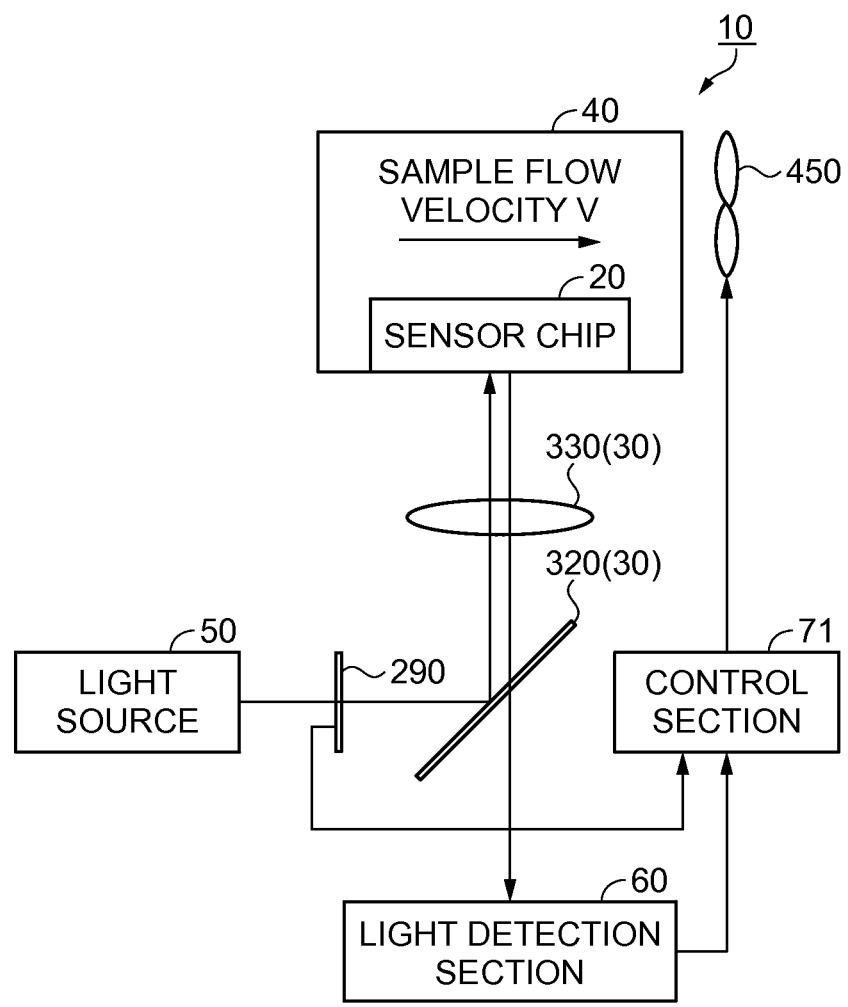
FIG. 1 is a block diagram showing a configuration of a detection device.

FIG. 1 is a block diagram showing a configuration of the detection device according to the present embodiment. As shown in FIG. 1, the detection device 10 has a sensor chip (an optical device) 20, a suction section 40, a light source 50, a light detection section 60, a control section 71, and a light intensity adjustment section 290. Between the sensor chip 20 and the light source 50, and between the sensor chip 20 and the light detection section 60, there is disposed an optical system 30. In the present embodiment, the fluid sample is, for example, air, and the inspection target material can be set to specific gas molecules (sample molecules) in the air, but is not limited thereto.

The suction section 40 is provided with a negative pressure generation section, for example, a fan 450, and sucks the fluid sample. The negative pressure generation section is not limited to the fan, but is only required to be what can generate a negative pressure in the suction section 40 to thereby suck in the fluid sample, such as a pump including a tube pump, a diaphragm pump, and so on. Further, the negative pressure generation section is provided with a function of making the inspection target material included in the fluid sample thus sucked be adsorbed by the sensor chip 20. The light emitted from the light source 50 irradiates the sensor chip 20 via the light intensity adjustment section 290 and the optical system 30. The light intensity adjustment section 290 is formed of an optical filter such as a light reducing filter. Further, the light intensity adjustment section 290 switches the optical filter to thereby adjust the intensity of the light irradiating the sensor chip 20. The optical system 30 is composed, for example, of a half mirror 320 and an objective lens 330. The light with which the sample molecules adsorbed to the sensor chip 20 is irradiated, and scattered by the sample molecules is enhanced due to the localized surface plasmon resonance (LSPR), and is emitted as the surface enhanced Raman scattering (SERS) light. The SERS light thus emitted passes through the objective lens 34 and the half mirror 32. Then, the light having passed therethrough is collected to the light detection section 60, and the light detection section 60 detects the light.

Figure 2:
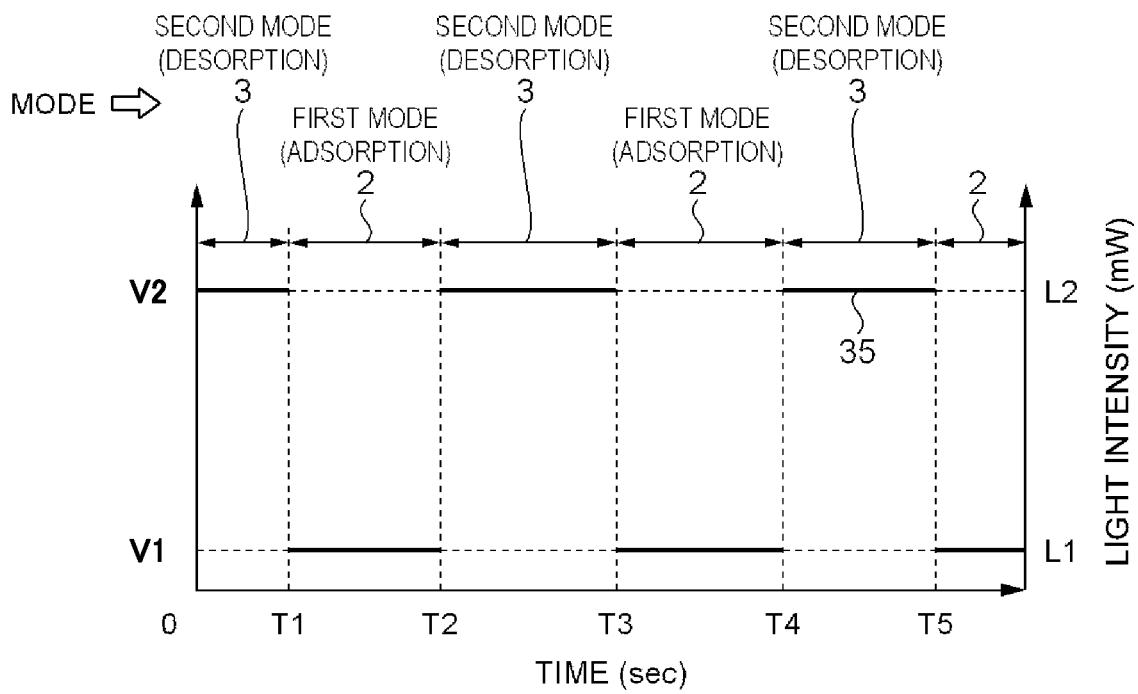
FIG. 2 is a graph for explaining a first mode and a second mode.

FIG. 2 is a graph for explaining a first mode and a second mode. In FIG. 2, switching lines 35 represent the transition in the flow rate and the light intensity. As indicated by the switching lines 35, the control section performs the control of switching between the first mode 2 and the second mode 3 based on the signal from the light detection section 60. Further, the control section 71 repeatedly switches between the second mode 3 and the first mode 2. Here, in the first mode 2, the inspection target material in the fluid sample is made to be adsorbed to the sensor chip 20, and the scattering light is detected by the light detection section 60. In the first mode 2, the control section 71 controls the fan 450 so that the flow velocity V of the fluid sample on the sensor chip 20 becomes V1 (m/min). Further, the control section controls the light source 50 so that the light intensity of the light emitted by the light source 50 becomes L1 (mW).

In the second mode 3, the inspection target material in the fluid sample is made to be desorbed from the sensor chip 20. In the second mode 3, the control section 71 controls the fan 450 so that the flow velocity becomes V2 (V2>V1). Further, the control section 71 controls the light source 50 so that the light intensity of the light emitted by the light source 50 becomes L2 (L2>L1). On this occasion, the control section 71 performs the drive control of the light reducing filter of the light intensity adjustment section 290 so as to be out of the light path.

The fan 450 provides the fluid sample transport rate of W1 (ml/min) in the first mode 2, and the fluid sample transport rate of W2 (ml/min) in the second mode 3, and fulfills W2>W1. The control of the fluid sample transport rate can be performed by controlling the fan 450, or by further disposing a valve or a shutter and varying the aperture area of the valve or the shutter. It is sufficient that the velocity of the fluid sample carrying the inspection target material on the sensor chip 20 can be controlled as a result of the control of the fan 450, the valve, the shutter, and so on.

In the case in which the light intensity of the light emitted from the light source 50 is L1 (mW) in the first mode 2, and the light intensity in the second mode 3 is L2 (mW), the light intensity adjustment section 290 fulfills L2>L1. The control of the light intensity of the light output from the light source 50 can be performed taking the adjustment by the light reducing filter as the target as described above, or by adjusting the light emission intensity of the light source itself. Any method can be adopted providing the light intensity on the sensor chip 20 can be varied as a result of the control.

Figure 3:
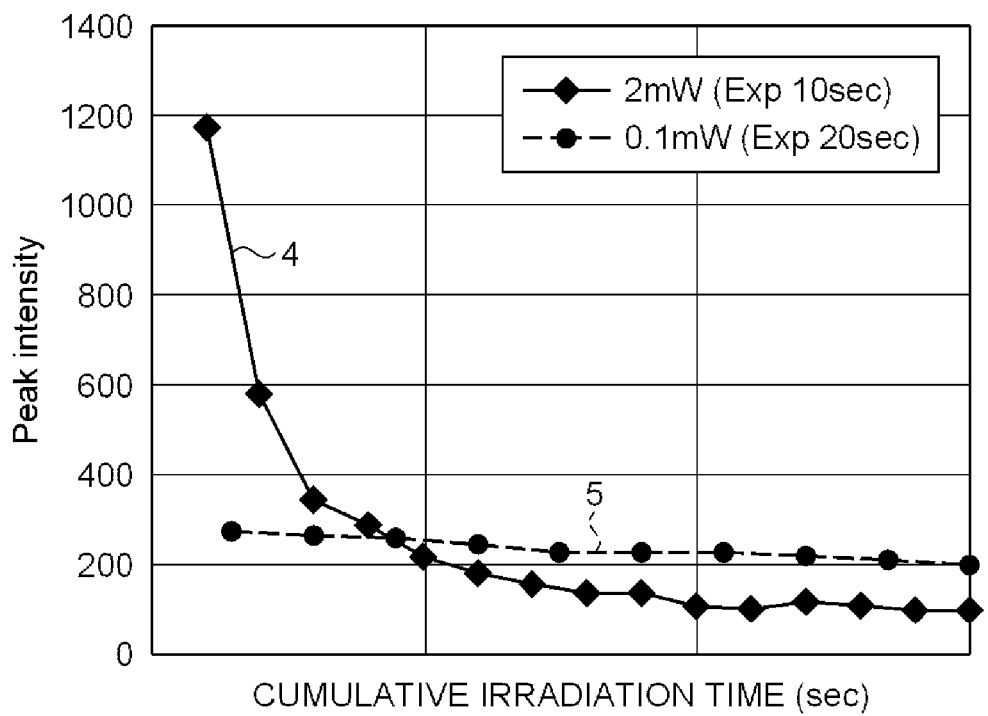
FIG. 3 is a characteristic chart showing a relationship between application of light energy and desorption of molecules from a sensor chip.

FIG. 3 is a characteristic chart showing a relationship between application of light energy and desorption of the inspection target molecules from the sensor chip. In FIG. 3, a first transition line 4 represents the transition of the desorption of the sample molecules from the sensor chip 20 when the light intensity is 2 mW. Further, a second transition line 5 represents the transition of the desorption of the sample molecules from the sensor chip 20 when the light intensity is 0.1 mW. The horizontal axis represents the cumulative irradiation time. The vertical axis represents the intensity of the signal detected by the light detection section 60, and is an amount corresponding to the density of the sample molecules adsorbed to the sensor chip 20.

In the first transition line 4 and the second transition line 5, the density of the sample molecules drops as the cumulative irradiation time increases. This shows the fact that the sample molecules are desorbed from the sensor chip 20. Further, the first transition line 4 has a higher variation than that of the second transition line 5. In other words, it shows the fact that by setting light intensity so as to fulfill L2>L1, the desorption performance of the sample molecules from the sensor chip 20 by the light energy application is improved.

It is conceivable that the reason that the desorption characteristics are improved is that the Joule heat due to the collective vibration (LSPR) of the free electrons developed in the metal nanoparticles increases by increasing the excitation light intensity, and therefore, the molecules adsorbed to the metal nanoparticles obtain the Joule heat, and thus can be desorbed therefrom. Therefore, by controlling the excitation light intensity, the desorption characteristics can be controlled.

In the present embodiment, it is possible to adsorb the inspection target material included in the fluid sample flowing at the flow velocity of V1 to the sensor chip 20 in the first mode 2. The first mode 2 can also be referred to as an adsorption mode. In the first mode 2, when irradiating the sensor chip 20 with the light via the light intensity adjustment section 290 with the light intensity of L1, the light reflecting the characteristics of the inspection target material adsorbed to the sensor chip 20 is generated. Then, by the light being collected to the light detection section 60, the light detection section 60 can detect the light from the sensor chip 20. In that context, the first mode 2 can also be referred to as an inspection mode in which the inspection is performed. On the other hand, in the second mode 3, the flow velocity is set to V2 higher than V1 in the first mode 2 (the adsorption mode or the inspection mode), and at the same time, the light intensity adjustment section 290 operates to set the intensity of the light from the light source 50 to L2 (L2>L1). Therefore, in the second mode 3, it is possible to efficiently desorb the inspection target material adsorbed to the sensor chip 20 due to the force of washing it away with the fluid and the light energy. Therefore, the second mode 3 can also be referred to as a desorption mode.

As described above, by performing the first mode 2 and the second mode 3 alternately, the inspection target material having once been adsorbed to the sensor chip 20 can be made to desorb. In such a manner, it is possible to clean up the sensor chip 20 after the inspection, and it becomes possible to repeatedly perform the subsequent inspection without leaving the influence of the previous inspection. For example, as shown in FIG. 2, by performing the second mode 3 prior to the first mode 2, it is possible to perform the inspection with the inspection target material adsorbed to the sensor chip 20 kept in a fresh state. By performing the first mode 2 and the second mode 3 alternately in a repeated manner, the real-time continuous inspection becomes possible.

Here, the values V1 and V2 as the respective flow velocities in the first mode 2 and the second mode 3 are each a flow velocity of the fluid sample on the sensor chip 20, and the fan 450 is driven so that the flow velocities V1, V2 can be achieved. On this occasion, in the case of performing the first mode 2 and the second mode 3 alternately in a repeated manner, it is also possible to stop the drive of the fan 450 in the first mode 2. In this case, the flow velocity V1 (V1≠0) of the fluid sample on the sensor chip 20 can be assured using the amount of flow and the inertia in the second mode 3. The switching between the first mode 2 and the second mode can be performed based on the output of the light detection section 60. Since the light detected by the light detection section 60 is changed between the first mode 2 and the second mode 3 due to the adsorption or desorption of the inspection target material, the light detection signal output by the light detection section 60 changes. Therefore, the adsorption condition of the sample molecules can be detected using the light detection signal.

Figure 4:
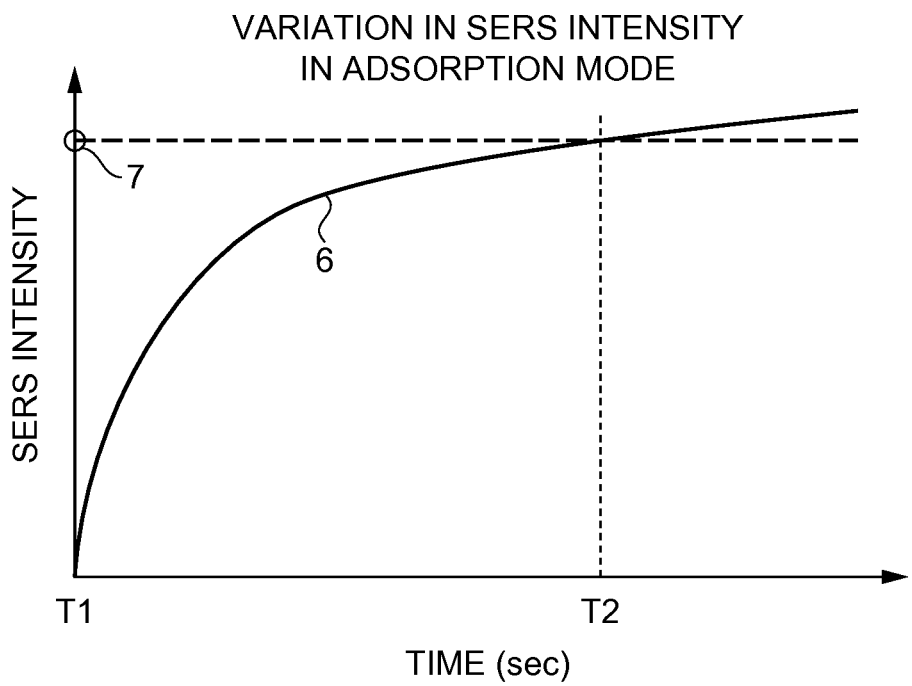
FIG. 4 is a graph showing the transition of the SERS intensity of sample molecules in a first mode.

The sensor chip 20 emits the surface enhanced Raman scattering (SERS) light using the localized surface plasmon resonance (LSPR). FIG. 4 is a graph showing transition of the SERS intensity of the sample molecules in the first mode. In FIG. 4, a first SERS intensity transition line 6 represents a variation in the SERS intensity of the sample molecules as the inspection target material output by the light detection section 60 in the first mode 2 (the adsorption mode or the inspection mode) in the period from the time T1 to the time T2. In the first mode 2 started at the time T1, the amount of the sample molecules adsorbed to the sensor chip 20 increases. Therefore, the SERS intensity increases in the first mode 2. Therefore, at the time T2 when the first SERS intensity transition line 6 rises to exceed a first determination level 7, the control section 71 determines to terminate the first mode 2. Then, the control section makes the transition from the first mode 2 to the second mode 3. In other words, the detection device 10 switches the mode from the first mode 2 to the second mode 3 when the signal level detected by the light detection section 60 exceeds the first determination level 7.

Figure 5:
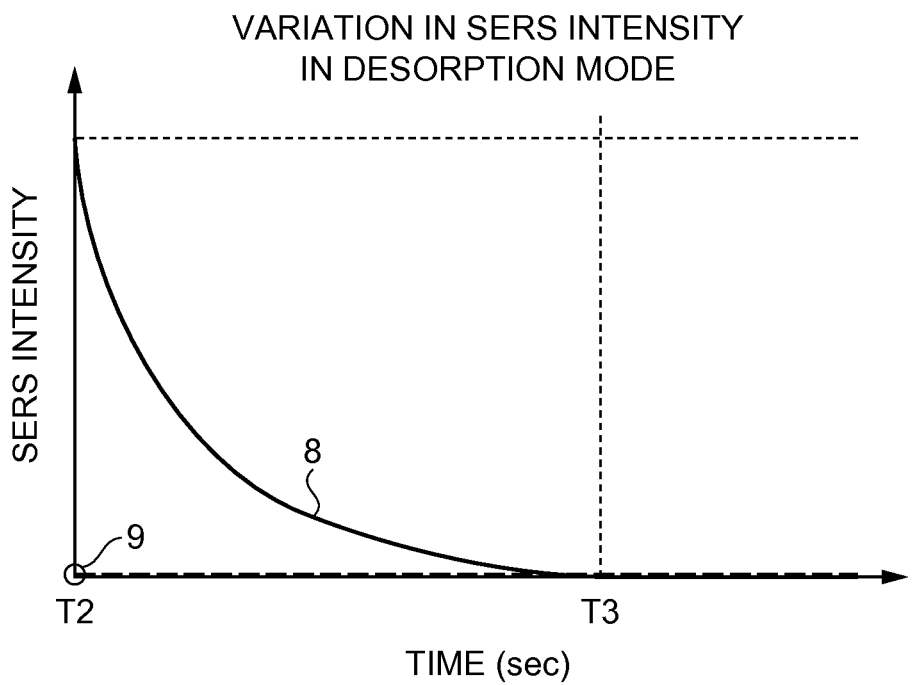
FIG. 5 is a graph showing the transition of the SERS intensity of the sample molecules in a second mode.

FIG. 5 is a graph showing transition of the SERS intensity of the sample molecules as the inspection target material in the second mode. A second SERS intensity transition line 8 represents the variation in the SERS intensity of the sample molecules output by the light detection section in the second mode 3 (the desorption mode). In the second mode 3 started at the time T2, the amount of the sample molecules desorbed from the sensor chip 20 increases. Therefore, the SERS intensity of the sample molecules decreases in the second mode 3. Therefore, the control section 71 determines to terminate the second mode 3 at the time T3 at which the SERS intensity falls below a second determination level 9 shown in FIG. 5. Then, the control section 71 makes the transition from the second mode 3 to the first mode 2. In other words, the detection device 10 switches the mode from the second mode 3 to the first mode 2 when the signal level detected by the light detection section 60 falls below the second determination level 9.

It should be noted that the SERS intensity is a value based on the number of photons received by a light receiving element of the light detection section 60. Although the first determination level 7 and the second determination level 9 are not particularly limited, the first determination level 7 is set to 200 in photon count, and the second determination level 9 is set to 100 in photon count, for example, in the present embodiment.

2. One Example of Principle and Structure of Light Detection

Figure 6A:
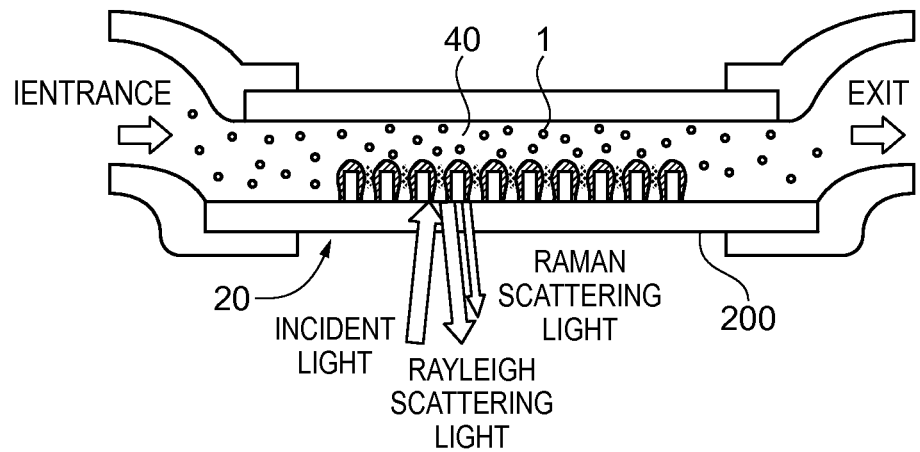
FIGS. 6A through 6C are schematic diagrams for explaining the detection principle of the Raman scattering light.
Figure 6B:
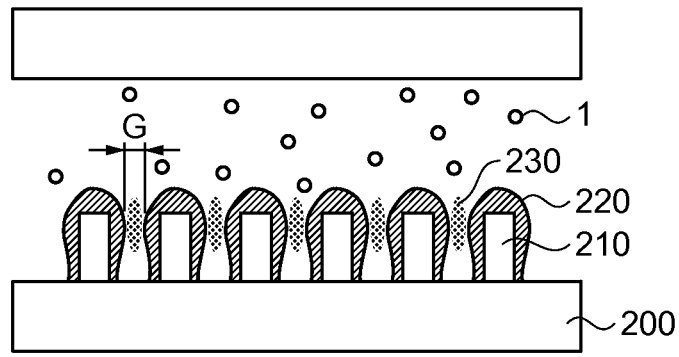
Figure 6C:
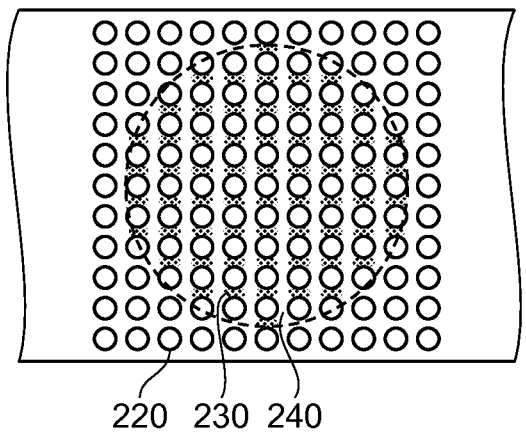

Then, explanatory diagrams of the detection principle of the Raman scattering light as one example of the light detection principle reflecting the sample will be shown using FIGS. 6A through 6C. FIGS. 6A through 6C are schematic diagrams for explaining the detection principle of the Raman scattering light. As shown in FIG. 6A, the sample molecules 1 as the inspection target material adsorbed to the sensor chip 20 are irradiated with the incident light (vibration frequency ν). In general, a most part of the incident light is scattered as the Rayleigh scattering light, and the vibration frequency ν or the wavelength of the Rayleigh scattering light is not varied with respect to the incident light. A part of the incident light is scattered as the Raman scattering light, and the vibration frequency (ν−ν' and ν+ν') or the wavelength of the Raman scattering light reflects the vibration frequency ν' (molecular vibration) of the sample molecules 1. In other words, the Raman scattering light is light reflecting the characteristics of the sample molecules 1. Although the part of the incident light excites the sample molecules 1 to thereby lose the energy, in some cases, the vibration energy of the sample molecules 1 is added to the vibration energy or the light energy of the Raman scattering light. Such a shift (ν') in the vibration frequency as described above is referred to as a Raman shift.

FIG. 6B is a schematic enlarged view of a substantial part of the sensor chip. In the case in which the incident light enters the flat surface of the substrate 200 as shown in FIG. 6A, a material transparent to the incident light is used for the substrate 200. The sensor chip 20 has a plurality of projections 210 made of a dielectric material as a first structure on the substrate 200. In the present embodiment, a resist is formed on the substrate 200 made of quartz, crystal, glass such as borosilicate glass, silicon, or the like as the dielectric material transparent with respect to the incident light, and then the resist is patterned using, for example, a deep ultraviolet (DUV) photolithography process. By etching the substrate 200 using the resist thus patterned, the plurality of projections 210 are arranged, for example, in a two-dimensional manner as shown in FIG. 6C. It should be noted that the substrate 200 and the projections 210 can also be made of respective materials different from each other.

As a second structure on the plurality of projections 210, the plurality of projections 210 is provided with metal nanoparticles (metal fine particles) 220 made of, for example, Au or Ag formed by, for example, evaporation or sputtering. As a result, the sensor chip 20 can be provided with a metal nanostructure having the projections in a range of 1 through 1000 nm. The metal nanostructure having the projections in a range of 1 through 1000 nm can be formed by a method of fixing the metal fine particles of the above size on the substrate by evaporation, sputtering, and so on, or a method of forming a metal film having an island structure on the substrate besides the method of processing the upper surface of the substrate 200 so as to have the projection structure (with the substrate material) of the above size.

As shown in FIGS. 6B and 6C, in the area 240 where the incident light enters the metal nanoparticles 220 arranged in a two-dimensional pattern, an enhanced electric field 230 is formed in the gap G between the metal nanoparticles 220 adjacent to each other. In particular, in the case of irradiating the metal nanoparticles 220 smaller than the wavelength of the incident light with the incident light, the electric field of the incident light affects the free electrons existing on the surface of the metal nanoparticles 220 to cause resonance. Thus, the electric dipoles due to the free electrons are excited in the metal nanoparticles 220, and the enhanced electric field 230 stronger than the electric field of the incident light is formed due to the localized surface plasmon resonance (LSPR). This phenomenon is unique to the electric conductor such as metal nanoparticles 220 smaller than the wavelength of the incident light.

In FIGS. 6A through 6C, when irradiating the sensor chip with the incident light, the surface enhanced Raman scattering (SERS) light occurs. Specifically, if the sample molecules 1 get into the enhanced electric field 230, the Raman scattering light due to the sample molecules 1 is enhanced by the enhanced electric field 230, and the signal intensity of the Raman scattering light increases. In such a surface enhanced Raman scattering, the detection sensitivity can be enhanced even with a minute amount of sample molecules 1.

The phenomenon called "adsorption" of the sample molecules described below is a phenomenon in which the number (partial pressure) of colliding molecules, namely the sample molecules colliding with the metal nanoparticles 220, is predominant, and includes one or both of physical adsorption and chemical adsorption. The term "desorption" means that the adsorption is released due to an external force. The adsorption energy depends on the kinetic energy of the gas molecules, and causes the "adsorption" phenomenon due to the collision if the adsorption energy exceeds a certain value. The adsorption does not require any external force. In contrast, the desorption requires an external force. Further, the suction of the fluid sample to the sensor chip 20 is to cause a suction flow in a flow channel having the sensor chip 20 disposed in the inside thereof in other words, and to make the fluid sample have contact with the sensor chip 20.

3. Specific Configuration of Detection Device

Figure 7:
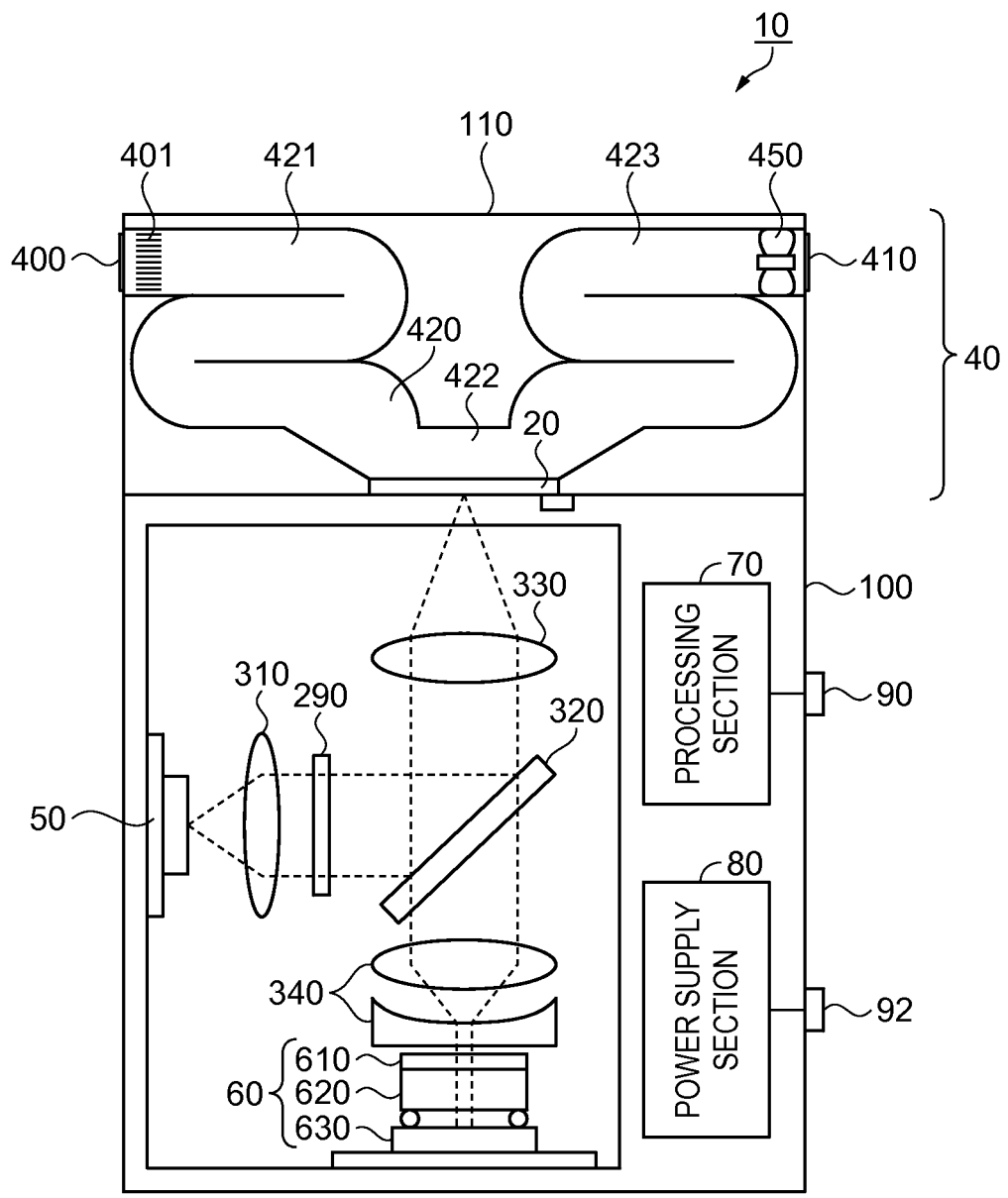
FIG. 7 is a schematic plan view showing a configuration of the detection device.

FIG. 7 is a schematic plan view showing the configuration of the detection device. As shown in FIG. 7, the detection device 10 has the sensor chip 20, the light intensity adjustment section 290 having the light reducing filter for switching the light intensity, the optical system 30, the suction section 40, the light source 50, the light detection section 60, and a processing section 70 including the control section 71.

The light source 50 is, for example, a laser, and a vertical cavity surface emitting laser can preferably be used therefore from the viewpoint of miniaturization, but the light source 50 is not limited thereto. The light from the light source 50 is collimated by a collimator lens 310 constituting the optical system 30. It is also possible to dispose a polarization control element on the downstream of the collimator lens 310 to thereby convert the light into a linearly polarized light. It should be noted that if the surface emission laser is adopted as the light source 50, and thus the light with the linearly polarized light can be emitted, the polarization control element can be eliminated.

The light collimated by the collimator lens 310 is guided toward the sensor chip 20 by the half mirror (the dichroic mirror) 320, then collected by the objective lens 330, and then enters the sensor chip 20. The sensor chip 20 is provided with the metal nanoparticles 220 shown in FIGS. 6A through 6C. The sensor chip 20 radiates, for example, the Rayleigh scattering light and the Raman scattering light due to the surface enhanced Raman scattering. The Rayleigh scattering light and the Raman scattering light from the sensor chip 20 pass through the objective lens 330, and are then guided toward the light detection section 60 by the half mirror 320.

The Rayleigh scattering light and the Raman scattering light from the sensor chip 20 are converged by collecting lenses 340, and are then input to the light detection section 60. In the light detection section 60, firstly, the lights reach an optical filter 610. The optical filter 610 (e.g., a notch filter) takes out the Raman scattering light. The Raman scattering light is further received by a light receiving element 630 via a spectroscope 620. The spectroscope 620 is formed of, for example, an etalon using the Fabry-Perot resonance, and can be made to have a variable pass frequency band. The wavelength of the light passing through the spectroscope 620 can be controlled (selected) by the control section 71. The Raman spectrum unique to the sample molecules 1 can be obtained by the light receiving element 630, and the Raman spectrum thus obtained and the data held previously are compared with each other for matching to thereby make it possible to identify the sample molecules 1.

The suction section 40 has an induction section 420 disposed between a suction port 400 and a discharge port 410. The fluid sample including the sample molecules 1 is introduced from the suction port 400 (carry-in entrance) into the inside of the induction section 420, and then discharged outside the induction section 420 from the discharge port 410. A dust removal filter 401 can be disposed on the suction port 400 side. The detection device 10 has the fan 450 for exhaust in the vicinity of the discharge port 410, and when activating the fan 450, the pressure (atmospheric pressure) inside a suction channel 421 of the induction section 420, a flow channel 422 in the vicinity of the sensor chip 20, and a discharge channel 423 falls. Thus, the sample molecules 1 is sucked in the induction section 420 together with the fluid sample. The fluid sample passes through the suction channel 421, and is then discharged from the discharge channel 423 via the channel 422 in the vicinity of the sensor chip 20. On this occasion, some of the sample molecules 1 is adsorbed to the surface (electric conductor) of the sensor chips 20.

The sample molecules 1 as the inspection target material can be assumed to be rare molecules of, for example, narcotic drugs, alcohol, and residual pesticides, pathogens such as viruses, and so on, and the present embodiment is particularly suitable for detecting such sample molecules 1 continuously in real time.

The detection device 10 has a housing 100, and has, for example, the optical system 30, the light source 50, the light detection section 60, and the processing section 70 inside the housing 100. Further, the detection section 10 can include a power supply section 80, a communication connection section 90, and a power supply connection section 92 inside the housing 100. The power supply section 80 supplies the light source 50, the light detection section 60, the processing section 70, the fan 450, and so on with the power from the power supply connection section 92. The power supply section 80 can be formed of, for example, a secondary battery, and can also be formed of a primary battery, an AC adapter, and so on. The communication connection section 90 is connected to the processing section 70, and transmits data, control signals, and so on to the processing section 70. The detection device 10 has a cover 110, and the cover 110 is capable of housing the sensor chip 20 and so on.

The processing section 70 can transmit commands to other sections such as the light detection section 60 or the fan 450 than the light source 50. Further, the processing section 70 is capable of performing a spectroscopic analysis using the Raman spectrum, and the processing section 70 is also capable of identifying the sample molecules 1 as the target object. It should be noted that the processing section 70 can transmit the detection result using the Raman scattering light, the spectroscopic analysis result using the Raman spectrum, and so on to, for example, external equipment (not shown) connected to the communication connection section 90.

Figure 8:
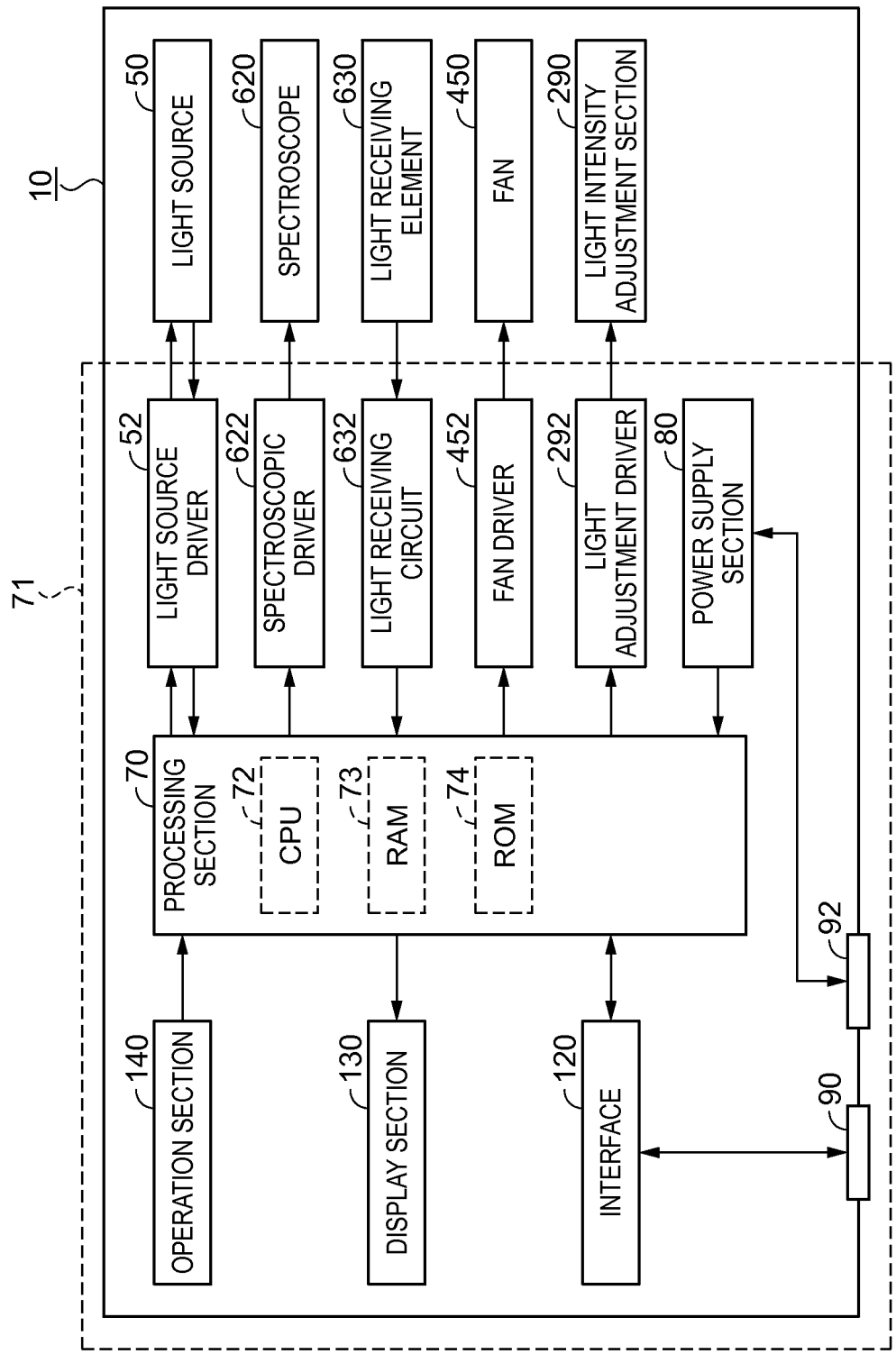
FIG. 8 is a block diagram of a control system of the detection device.

FIG. 8 is a block diagram of the control system of the detection device. As shown in FIG. 8, the detection device 10 is provided with the control section 71. The control section 71 can further include an interface 120, a display section 130, and an operation section 140. Further, the processing section 70 can include, for example, a central processing unit (CPU) 72, a random access memory (RAM) 73, a read only memory (ROM) 74. Further, the control section 71 can include, for example, a light source driver 52, a spectroscopic driver 622, a light receiving circuit 632, a fan driver 452, and a light adjustment driver 292.

The light source driver 52 drives the light source 50, and the spectroscopic driver 622 drives the spectroscope 620. The light-receiving circuit 632 drives the light receiving element 630 to amplify the signal corresponding to the light received by the light receiving element 630, and then outputs the result to the processing section 70. The fan driver 452 drives the fan 450. Further, the light adjustment driver 292 drives the light intensity adjustment section 290.

4. Explanation of Switching Between First Mode and Second Mode

Figure 9:
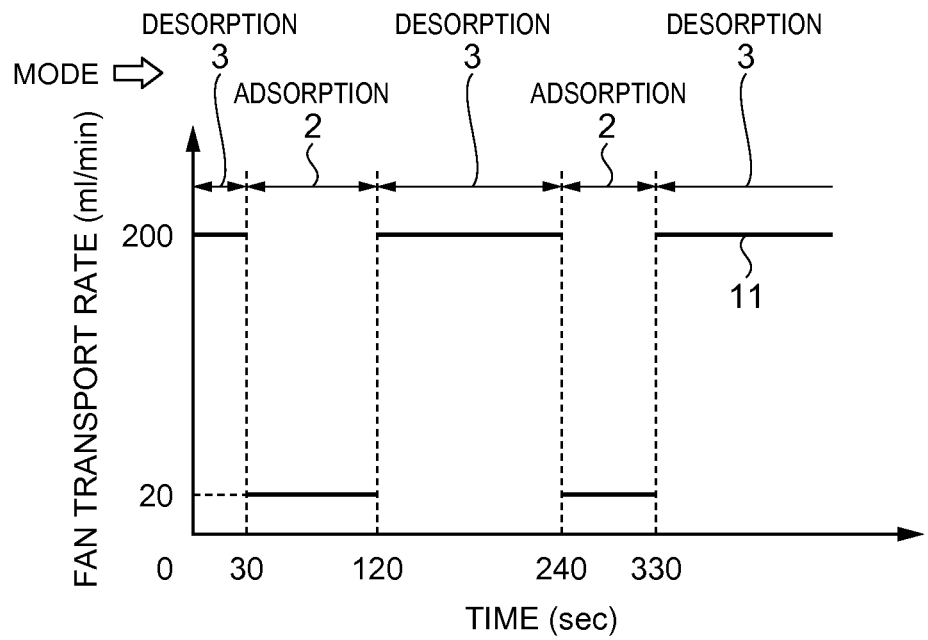
FIG. 9 is a time chart showing the first mode and the second mode.
Figure 10:
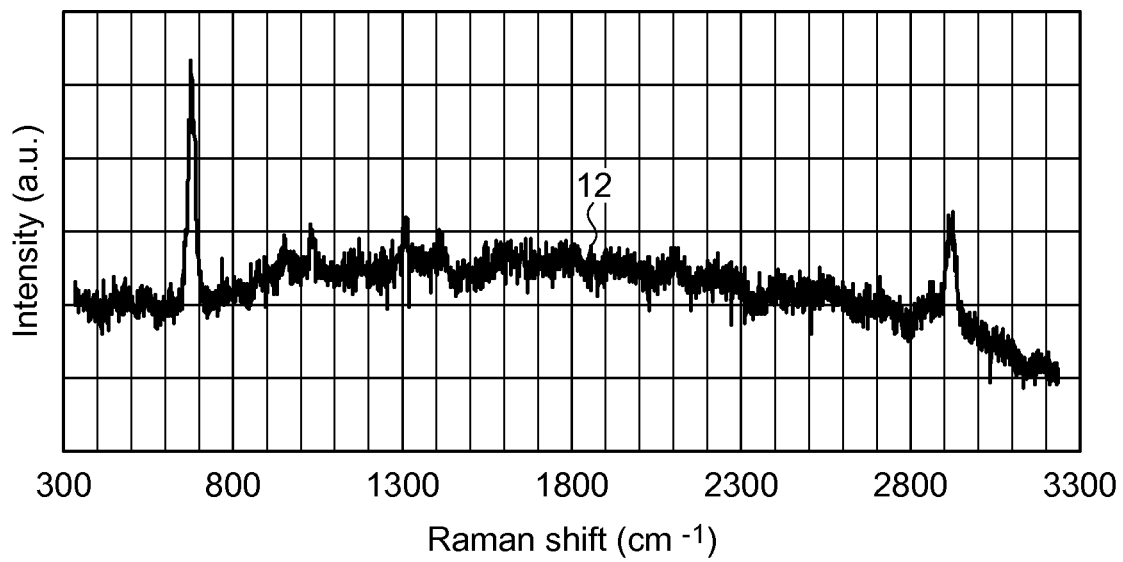
FIG. 10 is a graph showing an example of a measurement result of the sample molecules.

FIG. 9 is a time chart showing the first mode and the second mode, and FIG. 10 is a graph showing an example of a measurement result of the sample molecules 1 as the inspection target material. FIG. 10 shows a result of an actual measurement using dimethyl sulfide (DMS) gas molecules as the sample molecules performed in accordance with the switching lines 11 for switching between the first mode 2 (the adsorption mode) and the second mode 3 (the desorption mode) shown in FIG. 9. In FIG. 10, the horizontal axis represents the Raman shift ($cm^{-1}$), and the vertical axis represents the spectrum intensity. In the DMS molecules, the signal with the Raman shift of 676 $cm^{-1}$ is the strongest. In the following explanation, attention will be paid to the peak intensity with the Raman shift of 676 $cm^{-1}$. As the light source 50, a He—Ne laser with the excitation wavelength of 632.8 nm, and the intensity of 2 mW is used. The material of the sensor chip 20 is Ag. In the first mode 2 (the adsorption mode), the fluid transport rate W1 of the fan 450 is set to 20 ml/min, the light intensity L1 is set to 0.1 mW, and the measurement exposure time in the light detection section 60 is set to 20 seconds.

In the second mode 3 (the desorption mode), the fluid transport rate W2 of the fan 450 is set to 200 ml/min, the light intensity L2 is set to 2.0 mW, and the measurement exposure time in the light detection section 60 is set to 10 seconds. As indicated by the switching line 11, the experiment starts with the second mode 3 (the desorption mode) for 30 seconds. Thirty seconds later, the mode is switched to the first mode 2

(the adsorption mode) with W1 of 20 ml/min and L1 of 0.1 mW. FIG. 10 shows the SERS spectrum measured at 10 seconds after switching the mode. FIG. 10 is a graph showing the SERS spectrum. As shown in FIG. 10, in the first intensity distribution line 12, there can be confirmed a clear peak at the Raman shift of 676 cm$^{-1}$.

Figure 11:
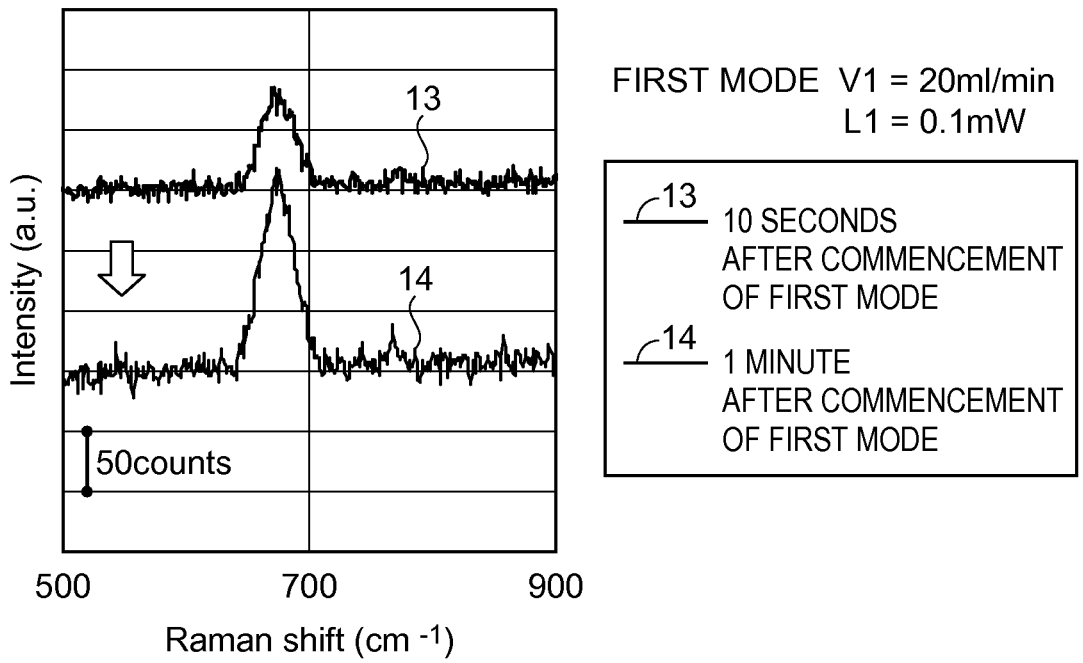
FIG. 11 is a graph showing the SERS spectrum.
Figure 12:
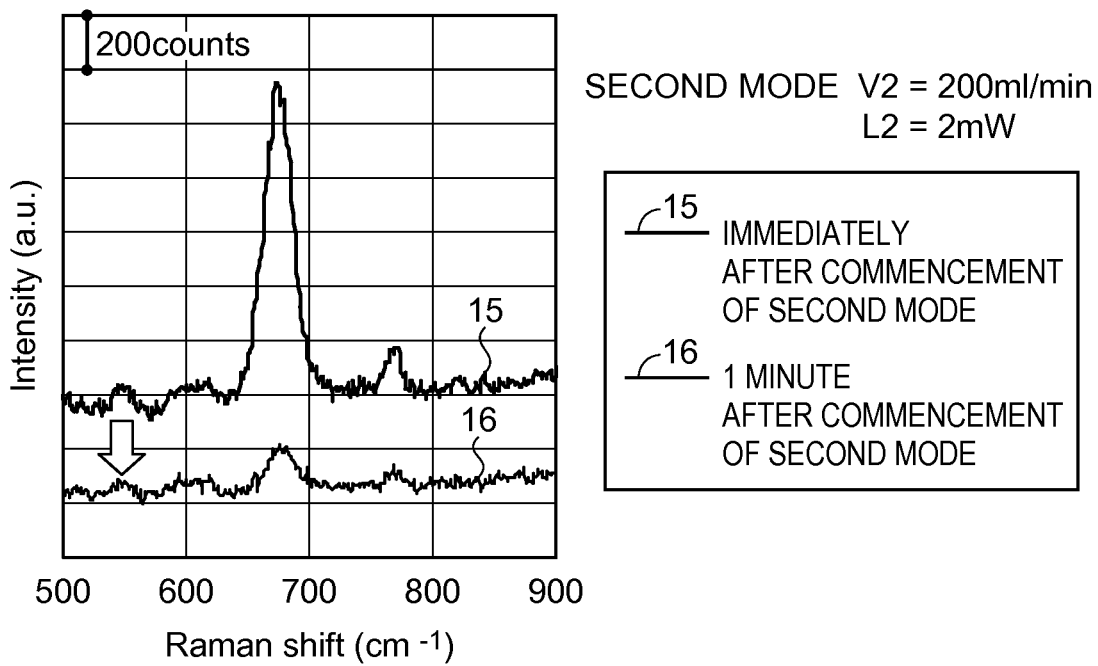
FIG. 12 is a graph showing the SERS spectrum.

FIGS. 11 and 12 are graphs showing the SERS spectrum, and show the area around the Raman shift of 676 cm$^{-1}$ in an enlarged manner. In FIG. 11, the second intensity distribution line 13 represents the distribution 10 seconds after commencement of the first mode 2 (the adsorption mode), and the third intensity distribution line 14 represents the distribution 1 minute after the commencement of the first mode 2 (the adsorption mode). The peak of the DMS molecules in the vicinity of the Raman shift of 676 cm$^{-1}$ is in a confirmable level but is still weak 10 seconds after the commencement of the first mode 2 (the adsorption mode) as indicated by the second intensity distribution line 13. By performing the SERS measurement setting the measurement mode 60 seconds after the commencement of the first mode 2 (the adsorption mode), it can be confirmed that the peak of the DMS molecules in the vicinity of the Raman shift of 676 cm$^{-1}$ becomes large and conspicuous. This proves that the adsorption has been advanced.

Subsequently, the mode is switched to the second mode 3 (the desorption mode) with the gas transport rate of W2=200 ml/min, and L2=2 mW, and the desorption is promoted. In FIG. 12, the fourth intensity distribution line 15 represents the distribution immediately after commencement of the second mode 3 (the desorption mode), and the fifth intensity distribution line 16 represents the distribution 1 minute after the commencement of the second mode 3 (the desorption mode). In the spectrum measured immediately after the commencement of the second mode 3 (the desorption mode), the clear and strong peak can be confirmed as indicated by the fourth intensity distribution line 15. It should be noted that the reason that the intensity becomes higher than in the adsorption mode is that the excitation light intensity increases from 0.1 mW to 2 mW, and is not the increase in the adsorbed molecules. When one minute has elapsed from the commencement of the second mode 3, the peak of the DMS having been conspicuous is dramatically attenuated as indicated by the fifth intensity distribution line 16. It should be noted that the times described here is nothing more than an example, and need to appropriately be changed with the material of the sensor chip 20 and the sample molecules. Therefore, it is preferable to set the appropriate times by previously performing experiments. In the example of the switching lines 11, although the initial second mode 3 (the desorption mode) is set to 30 seconds, the subsequent first mode 2 (the adsorption mode) is set to 90 seconds, and the further second mode 3 (the desorption mode) is set to 120 seconds, in reality, as shown in FIGS. 2, 4 and 5, the mode switching is performed by comparing the SERS intensity with the first determination level 7 and the second determination level 9.

Modified Examples

5. Modified Example Using Reference Molecules In Combination

Then, one modified example of the detection device as an embodiment of the invention will be explained with reference to FIGS. 13 through 18. The present modified example is different from the embodiment described above in the point that a reference molecule storage chamber is provided. It should be noted that the explanation on the point the same as in the embodiment described above will be omitted.

5.1. Overall Structure

It is assumed that TNT molecules as component molecules of an explosive are detected as the inspection target material in, for example, a port or a harbor. In normal cases, the TNT molecules do not exist in the air. Therefore, if the detection along the method of the embodiment described above taking the TNT molecules as the sample molecules, it takes eternity to end the first mode 2 (the adsorption mode). This is because there is high probability that in normal cases the SERS intensity of the TNT molecules does not exceed the first determination level 7 even if the first mode 2 (the adsorption mode) is set. On this occasion, the second mode 3 (the desorption mode) is not started. Therefore, the surface of the sensor chip 20 is contaminated with other molecules, and the adsorption sites located on the surface of the sensor chip 20 are saturated, and it becomes unachievable to adsorb the TNT molecules as the inspection target material. Therefore, the reliability of the determination that no sample molecule surely exists or that an infinitesimal quantity of sample molecules 1 exists is degraded. According to the present embodiment, it becomes possible to repeatedly make transition to the breakaway mode even in the case of the material, which does not exist, or only an infinitesimal quantity of which exists.

Figure 13:
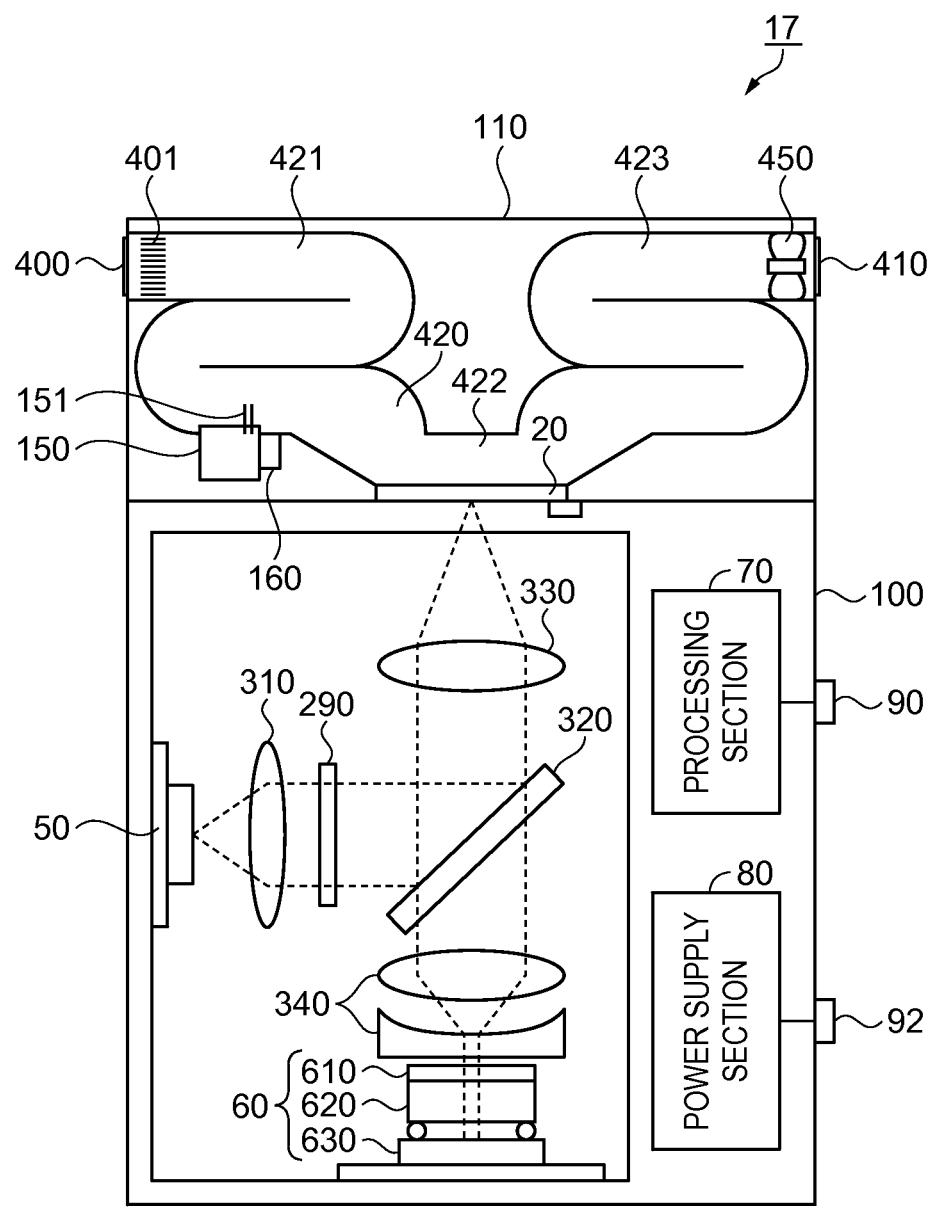
FIG. 13 is a schematic plan view showing a configuration of the detection device according to a modified example.

FIG. 13 is a schematic plan view showing the configuration of the detection device according to the modified example. In FIG. 13, the detection device 17 detects the reference molecules in addition to the sample molecules 1 in the fluid sample, and switches between the first mode 2 and the second mode 3 based on the detection signal of the sample molecules and the reference molecules. The detection device 17 is provided with a reference molecule storage chamber 150 disposed on the upstream side of the sensor chip 20 of the suction section 40 in addition to the detection device 10 shown in FIG. 7.

The reference molecules are stored in the reference molecule storage chamber 150, and the reference molecules are in vapor form, for example. The reference molecule storage chamber 150 has an ejection port 151 for ejecting the reference molecules to the induction section 420. The reference molecule storage chamber 150 is provided with an ejection drive section 160. The ejection drive section 160 ejects a certain amount of reference molecules from the ejection port 151 to the induction section 420 when starting the first mode 2 (the adsorption mode). The ejection drive section 160 adjusts the ejection time in accordance with the flow speed of the gas flowing through the suction channel 421 and the vapor pressure inside the reference molecule storage chamber 150. It is arranged that the ejection drive section 160 thus supplies the certain amount of reference molecules from the ejection port 151 into the atmosphere. A supply section composed of the reference molecule storage chamber 150, the ejection port 151, the ejection drive section 160, and so on is an example of a supply section for supplying the reference molecules. Here, the reference molecules needs to fulfill the requirement that the Raman scattering light can be detected at a wavelength different from that of the sample molecules. It should be noted that although it is assumed that the reference molecules are in vapor form on assumption that the fluid sample is in a gaseous state, if the fluid sample is a liquid, the reference molecules are preferably in liquid form.

The spectroscope 620 is a device from which the light having a variable wavelength band is taken out such as an etalon, or a device from which a plurality of lights which different wavelength can simultaneously be taken out such as a diffraction grating, and is a device capable of taking out the Raman scattering light of both of the sample molecules and the reference molecules. The light receiving element 630 is an element for detecting the SERS intensity of both of the sample molecules and the reference molecules.

Figure 14:
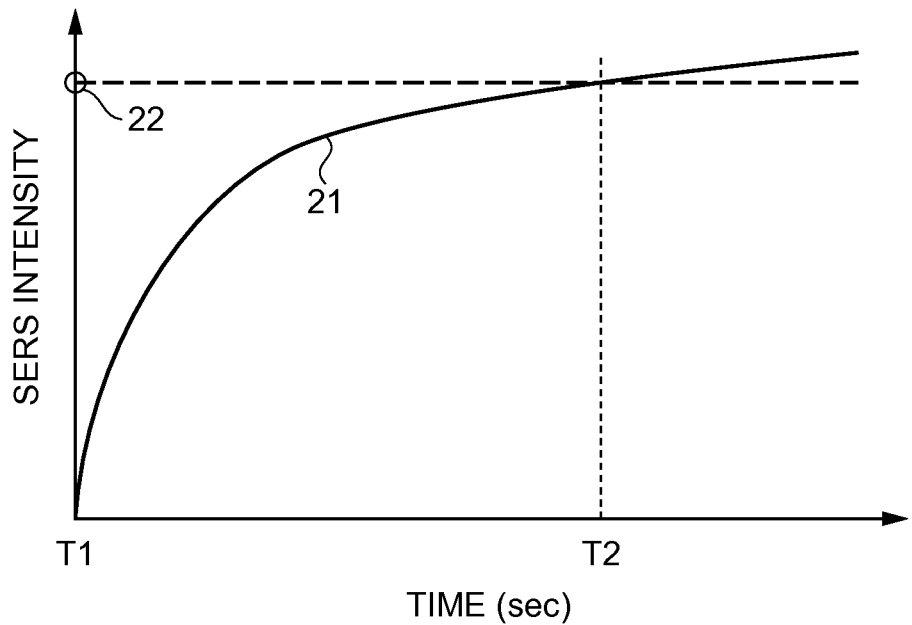
FIG. 14 is a graph showing the transition of the SERS intensity of the sample molecules in the first mode.

FIG. 14 is a graph showing the transition of the SERS intensity of the reference molecules in the first mode, and shows the output of the light detection section 60 during the period of supplying the reference molecules from the reference molecule storage chamber 150. In FIG. 14, the third SERS intensity transition line 21 represents the variation in the SERS intensity of the reference molecules output by the light detection section 60 during the period in which the reference molecules are continuously supplied from the reference molecule storage chamber 150. At the time T1, a certain amount of the reference molecules is supplied from the ejection port 151 into the fluid sample. Then, as indicated by the third SERS intensity transition line 21, the reference molecules adsorbed by the sensor chip 20 increase with time elapsed from the commencement of the supply of the reference molecules. Therefore, if the supply of the reference molecules is performed in the first mode 2 (the adsorption mode), the SERS intensity of the reference molecules increases. Therefore, at the time T2 when the SERS intensity of the reference molecules exceeds the third determination level 22 indicated by the third SERS intensity transition line 21, the determination of terminating the first mode 2 can be made. The time for stopping the supply of the reference molecules (reference sample) can be set to the time of terminating the first mode 2. Specifically, even if the signal level reflecting the sample molecules 1 as the inspection target material is lower than the first determination level 7, the control section 71 switches the mode from the first mode 2 to the second mode 3 when the signal level reflecting the reference molecules exceeds the third determination level 22.

Figure 15:
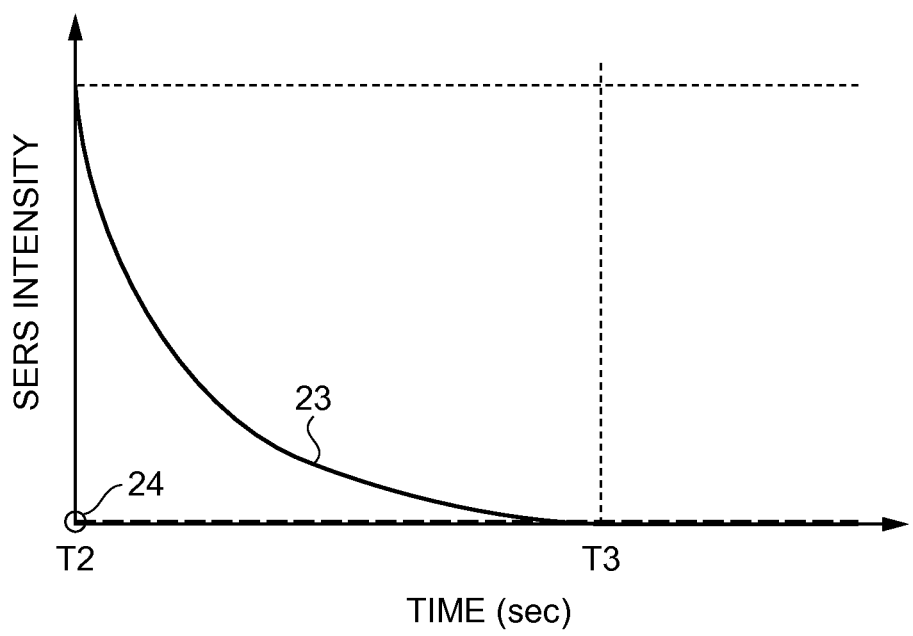
FIG. 15 is a graph showing the transition of the SERS intensity of the sample molecules in the second mode.

FIG. 15 is a graph showing transition of the SERS intensity of the reference molecules in the second mode. In FIG. 15, the fourth SERS intensity transition line 23 represents the variation in the SERS intensity of the reference molecules similarly output by the light detection section 60 in the second mode 3 (the desorption mode). As indicated by the fourth SERS intensity transition line 23, in the second mode 3 started at the time T2, the amount of the reference molecules desorbed from the sensor chip 20 increases since no reference molecules are supplied, and moreover, the flow velocity is high. Therefore, the SERS intensity decreases as time elapses in the second mode 3. Therefore, at the time T3 when the SERS intensity of the reference molecules falls below the fourth determination level 24, the determination of terminating the second mode 3 can be made. Specifically, even if the signal level from the light detection section 60 corresponding to the sample molecules 1 as the inspection target material is higher than the second determination level 9, the control section 71 switches the mode from the second mode 3 to the first mode 2 when the signal level from the light detection section 60 corresponding to the reference molecules falls below the fourth determination level 24.

Figure 16:
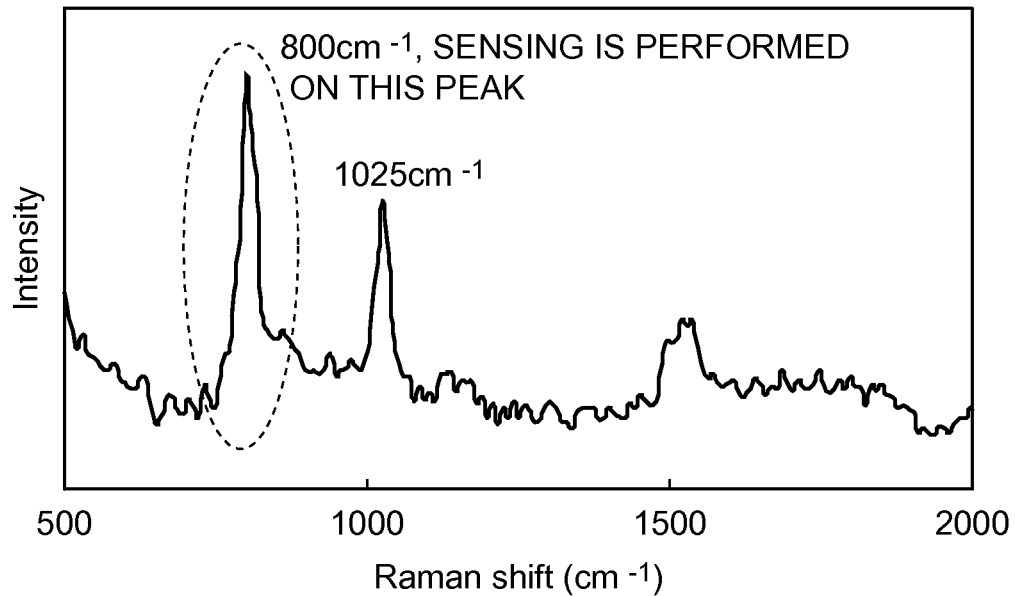
FIG. 16 is a graph showing the SERS spectrum of TNT molecules.

Here, the reference molecules can be composed of the molecules including at least one of a hetero ring, a benzene ring, a COOH group, an OH group, a CHO group, an S atom, and an N atom. For example, pyridine can be cited as an example of the hetero ring. FIG. 16 is a graph showing the SERS spectrum of TNT molecules. As shown in FIG. 16, the TNT molecules have a peak in the vicinity of 800 cm$^{-1}$. Therefore, since the pyridine as the reference molecules has sharp peaks at 1010 cm$^{-1}$ and 1035 cm$^{-1}$, in the case in which the TNT molecules are the sample molecules, it is possible to prevent the peaks of the Raman scattering lights of the TNT molecules and the reference molecules from overlapping each other.

5.2. Second Experimental Example

Figure 17:
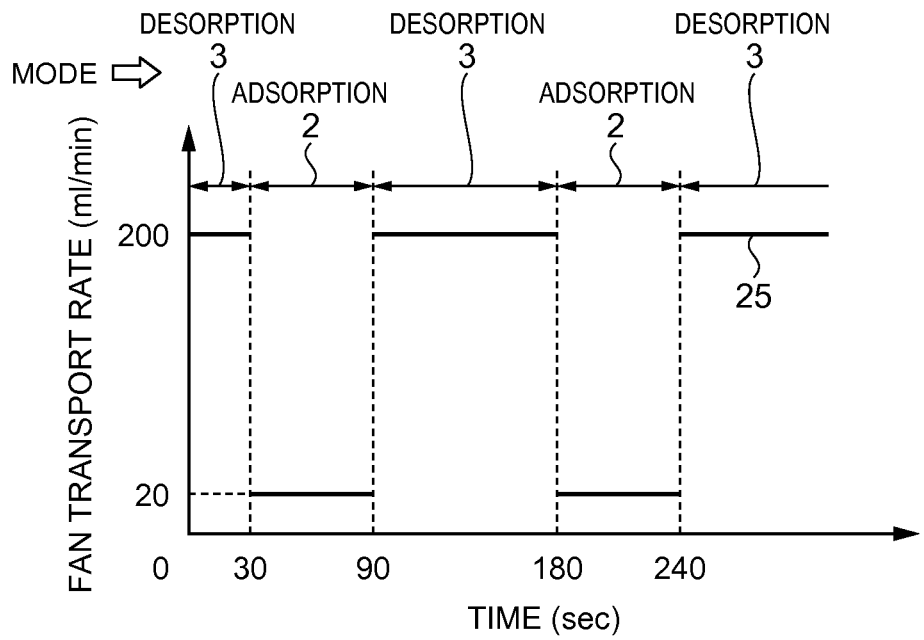
FIG. 17 is a graph for explaining the first mode and the second mode.
Figure 18:
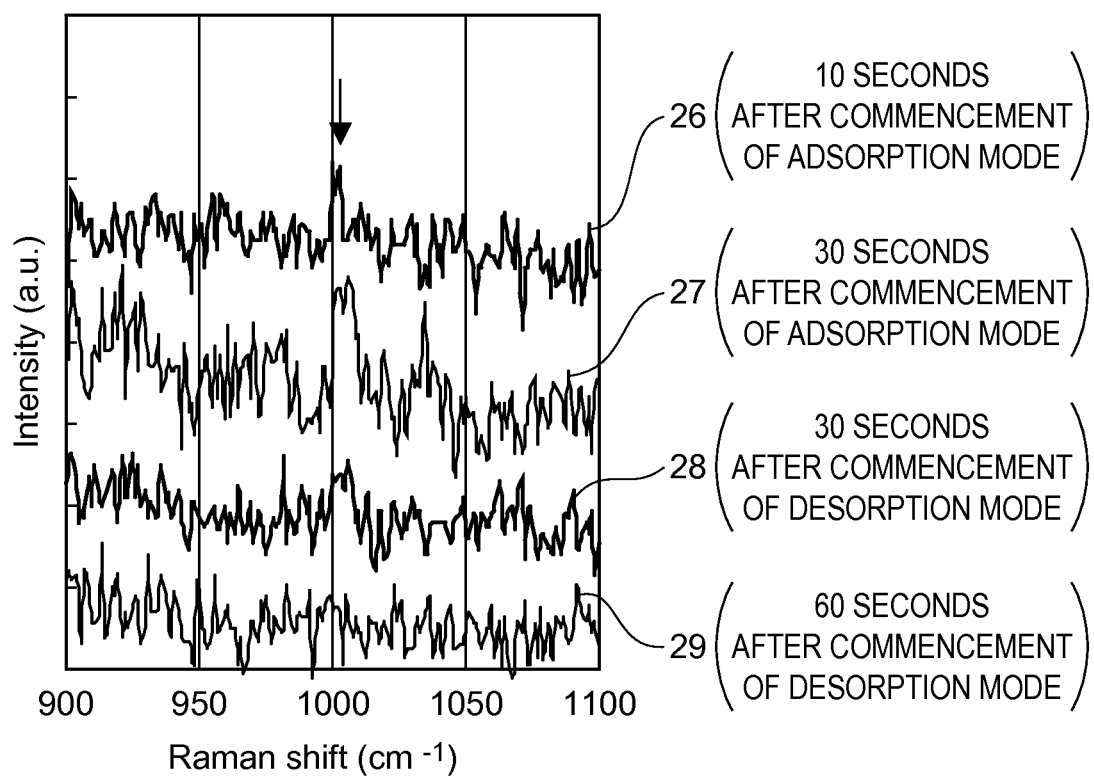
FIG. 18 is a graph showing the SERS spectrum.

FIG. 17 is a graph for explaining the first mode and the second mode. As shown in FIG. 17, an experiment has been conducted along the switching lines 25 of performing the first mode 2 (the adsorption mode) and the second mode 3 (the desorption mode) alternately. It should be noted that the sample molecules 1 as the inspection target material are not particularly assumed in the second experimental example. As the light source 50, a He—Ne laser with the excitation wavelength of 632.8 nm, and the intensity of 2 mW is used. As the material of the sensor chip 20, Ag is adopted. In the first mode 2 (the adsorption mode), the fluid transport rate W1 of the fan 450 is set to 20 ml/min, the excitation light intensity L1 is set to 0.1 mW on the sensor chip 20, and the measurement exposure time in the light detection section 60 is set to 20 seconds. In the second mode 3 (the desorption mode), the fluid transport rate W2 of the fan 450 is set to 200 ml/min, the excitation light intensity L2 is set to 2 mW on the sensor chip 20, and the measurement exposure time in the light detection section 60 is set to 10 seconds. As indicated by the switching lines 25, the experiment starts with the second mode 3 (the desorption mode) for 30 seconds. Thirty seconds later, the mode is switched to the first mode 2 (the adsorption mode). The conditions of the first mode 2 (the adsorption mode) are W1=20 ml/min and L1=0.1 mW. The supply of pyridine as the reference molecules is started immediately after switching the mode. The supply time of the reference molecules is set to 10 seconds. FIG. 18 shows the SERS spectrum of the pyridine molecules thus measured. FIG. 18 is a graph showing the SERS spectrum, and shows the measurement result with the switching lines 25 using the pyridine molecules as the reference molecules. The sixth intensity distribution line 26 represents the SERS spectrum 10 seconds after switching the mode to the first mode 2 (the adsorption mode). The seventh intensity distribution line 27 represents the SERS spectrum 30 seconds after switching the mode to the first mode 2 (the adsorption mode). The eighth intensity distribution line 28 represents the SERS spectrum 30 seconds after switching the mode to the second mode 3 (the desorption mode). The ninth intensity distribution line 29 represents the SERS spectrum 60 seconds after switching the mode to the second mode 3 (the desorption mode).

As indicated by the sixth intensity distribution line 26 and the seventh intensity distribution line 27, the peak of the pyridine molecules in the vicinity of 1010 cm$^{-1}$ can clearly recognized at both timings 10 seconds and 30 seconds after the commencement of the adsorption mode. Subsequently, the driving conditions of the detection device 17 are switched to the second mode 3 (the desorption mode). Thus, the mode is switched to the desorption mode with W2=200 ml/min and L2=2 mW, and the desorption of the pyridine molecules from the sensor chip 20 is promoted. As indicated by the eighth intensity distribution line 28, attenuation is observed in the spectrum measured 30 seconds after the commencement of the desorption mode. As indicated by the ninth intensity distribution line 29, the peak is further dramatically attenuated 60 seconds after the commencement of the desorption mode. It should be noted that the times described here are nothing more than an example, and need to appropriately be changed with the material of the sensor chip 20 and the sample molecules.

In the experimental example of the switching lines 25 shown in FIG. 17, the initial desorption mode is set to 30 seconds, the subsequent adsorption mode is set to 60 seconds, and the further desorption mode is set to 90 seconds. In reality, as shown in FIGS. 14 and 15, the mode switching is performed by comparing the SERS intensity of the reference molecules with the third determination level 22 and the fourth determination level 24.

The entire disclosure of Japanese Patent Application No. 2011-099243, filed Apr. 27, 2011 is expressly incorporated by reference herein.

What is claimed is:

1. A detection device comprising:
   a sensor chip;
   a suction section adapted to suck a fluid sample including a sample molecule to thereby adsorb the fluid sample to the sensor chip;
   a light source adapted to irradiate the sensor chip with light;
   a light intensity adjustment section adapted to adjust intensity of the light irradiating the sensor chip;
   a light detection section adapted to detect the sample molecule using light reflecting the sample molecule adsorbed on the sensor chip; and
   a control section adapted to control the suction section and the light intensity adjustment section,
   wherein assuming that a flow velocity of the fluid sample on the sensor chip in a first mode including a period in which the light detection section performs the detection is V1, and the flow velocity of the fluid sample on the sensor chip in a second mode is V2, the suction section controls the flow velocity of the fluid sample so that V2>V1 is fulfilled,
   assuming that the intensity of the light on the sensor chip from the light source in the first mode is L1, and the light intensity on the sensor chip in the second mode is L2, the light intensity adjustment section controls the light intensity so that L2>L1 is fulfilled, and
   the control section switches between the first mode and the second mode based on a signal from the light detection section.

2. The detection device according to claim 1, wherein the sensor chip generates Raman scattering light of the fluid sample, and
   the light detection section detects the Raman scattering light of an inspection target material, which can exist in the fluid sample.

3. The detection device according to claim 2, wherein the light intensity adjustment section includes an optical filter, and adjusts the light intensity by switching the optical filter.

4. The detection device according to claim 2, wherein the suction section includes a negative pressure generation section, and
   the control section controls a drive condition of the negative pressure generation section.

5. The detection device according to claim 2, wherein the control section compares a level of the signal output by the light detection section with a first determination level, and when the level of the signal exceeds the first determination level, the control section performs switching from the first mode to the second mode.

6. The detection device according to claim 5, wherein the control section performs switching from the second mode to the first mode when the level of the signal from the light detection section falls below a second determination level.

7. The detection device according to claim 2, further comprising:
   a supply section adapted to supply the sensor chip with a reference sample via the fluid sample in the first mode,
   wherein the light detection section detects light reflecting the reference sample at a wavelength different from that of the inspection target material, which can exist in the fluid sample, and
   the control section performs switching from the first mode to the second mode when a level of the signal reflecting the reference sample exceeding a third determination level despite the signal reflecting the inspection target material is lower than the first determination level.

8. The detection device according to claim 7, wherein the control section performs switching from the second mode to the first mode when a signal level from the light detection section corresponding to the reference sample falls below a fourth determination level despite the level of the signal from the light detection section corresponding to the sample molecule as the inspection target is higher than the second determination level.

9. The detection device according to claim 7, wherein the supply section supplies a constant amount of the reference sample during the first mode.

10. The detection device according to claim 7, wherein the reference sample is a molecule including at least one of a hetero ring, a benzene ring, a COOH group, an OH group, a CHO group, an S atom, and an N atom.

11. The detection device according to claim 2, wherein the control section at least switches between the second mode and the first mode in a repeated manner.

* * * * *